United States Patent [19]
Codkind

[11] Patent Number: 4,995,119
[45] Date of Patent: Feb. 26, 1991

[54] PROTECTIVE GLOVE OR GLOVE LINERS

[76] Inventor: Doris Codkind, 10 Houston Ave., Monroe, N.Y. 10950

[21] Appl. No.: 273,450

[22] Filed: Nov. 18, 1988

[51] Int. Cl.⁵ .............................................. A41D 19/00
[52] U.S. Cl. ....................................... 2/163; 2/161 R
[58] Field of Search ............... 2/159, 163, 160, 161 R, 2/164, 168, 21, 167, 169; 128/878, 879, 880

[56] References Cited

U.S. PATENT DOCUMENTS

| | | | |
|---|---|---|---|
| 325,968 | 9/1885 | Rawlings | 2/164 X |
| 732,360 | 6/1903 | Lindsay | 2/168 |
| 1,689,212 | 10/1928 | Picker | 2/164 X |
| 1,989,717 | 2/1935 | Szegvari | 2/168 |
| 2,232,396 | 2/1941 | Lee et al. | 2/21 |
| 2,379,624 | 5/1944 | Chisnell | 2/21 X |
| 3,511,242 | 5/1970 | Agnone | 2/21 |
| 3,633,216 | 1/1972 | Schonholtz | 2/168 |
| 3,732,575 | 5/1973 | Pakulak | 2/161 R |
| 4,507,807 | 4/1985 | Karkanen | 2/163 X |
| 4,559,646 | 12/1985 | Ertl | 2/161 R X |
| 4,663,783 | 5/1987 | Obayashi | 2/164 X |
| 4,696,065 | 9/1987 | Elenteny | 2/168 |
| 4,771,482 | 9/1988 | Shlenker | 2/161 R |
| 4,873,998 | 10/1989 | Joyner | 2/16 X |

FOREIGN PATENT DOCUMENTS

| | | | |
|---|---|---|---|
| 509545 | 6/1955 | Italy | 2/168 |
| 0120668 | 9/1979 | Japan | 2/163 |
| 0326719 | 3/1930 | United Kingdom | 604/349 |
| 612236 | 11/1948 | United Kingdom | 2/161 R |

*Primary Examiner*—Werner H. Schroeder
*Assistant Examiner*—Sara M. Current
*Attorney, Agent, or Firm*—Millen, White & Zelano

[57] ABSTRACT

A protective glove, for use alone or as a liner for a second type of glove, comprises flexible finger pads adhesively secured within a flexible outer glove, optionally comprising an additional inner thin flexible glove adhesively secured within the finger pads. The gloves provide added protection for the fingertips and nails from penetration of the gloves by foreign objects.

13 Claims, 2 Drawing Sheets

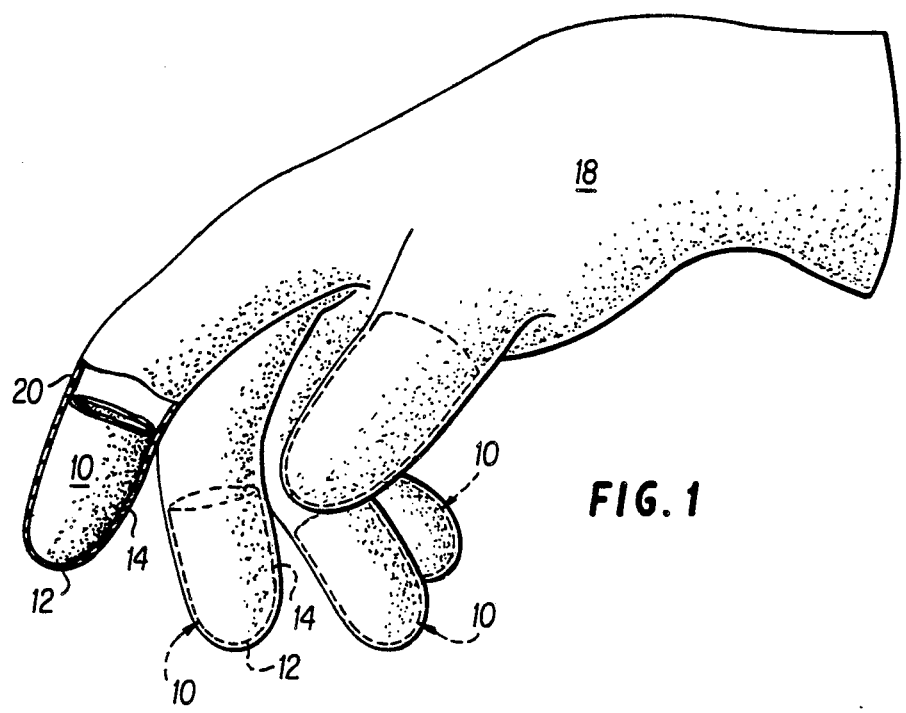
FIG. 1
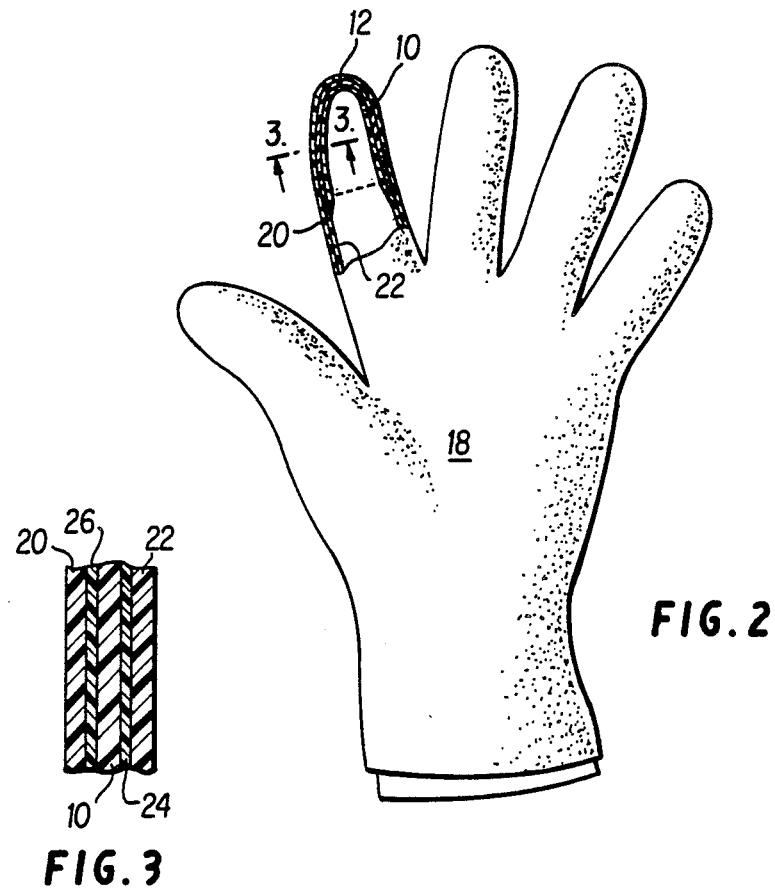
FIG. 2
FIG. 3

PROTECTIVE GLOVE OR GLOVE LINERS

BACKGROUND OF THE INVENTION

The present invention relates to protective gloves or glove liners with flexible rubber finger pads designed to provide additional protection to the distal ends of the fingers and fingernails without sacrificing flexibility in the remainder of the glove.

Fingernails and fingertips get jammed against furniture, appliances and all manner of obstacles while hands are in use. When gardening, sharp small stones or wood slivers penetrate burlap or canvas gloves. Thorns from bushes often lodge under the fingernails. Chipping and breaking of nails is a common occurrence during this type of handwork. Use of conventional gloves only provides minimal protection to hands and nails.

Similarly, the vinyl gloves used by, for example, workers in the medical and clinical laboratory professions are often subject to failure, especially at the fingertip area. This is due to the combination of thinness of the gloves required to allow fine control, sensitivity of touch and dexterity in the manipulations their hands must be able to do, and the sharp instruments, e.g., scalpels, scissors and needles, with which they must work. The consequences of nicks and needle sticks, which are very common occurrences in these fields, has become in recent years more than a mere annoyance. In an effort to avoid these injuries and, therefore, avoid exposure to various diseases, especially AIDS, it is of great concern that hand protection be available which combines improved safety with the required flexibility.

SUMMARY OF THE INVENTION

The present invention provides a solution to the above-mentioned problems by incorporating the use of heavy but flexible rubber finger pads, for example, of the type used for counting paper, inserted and anchored into the tips of close-fitting vinyl gloves, for example, surgical gloves. This provides a removable liner which can be employed with a variety of conventional outer gloves, i.e., waterproof housecleaning-type rubber gloves and burlap or canvas gardening gloves, in order to provide added protection to the fingertips and fingernails while they are performing functions which might result in stabbing, sticking, jamming or like types of injury.

Alternatively, the finger pads may be sandwiched between two gloves for added protection and to facilitate quick removal of the hand from the liner.

Either embodiment of the invention may be used as a glove itself, for example, when used to replace regular surgical-type vinyl gloves, in addition to its use as a liner for other outer gloves.

Upon further study of the specification and appended claims, further objects and advantages of this invention will become apparent to those skilled in the art.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein:

FIG. 1 is a perspective view, partially in section, of a first embodiment of the protective glove in accordance with the instant invention;

FIG. 2 is a view of a second embodiment of the invention showing the palm side of the protective glove with a portion of the index finger stall broken away to show the triple layer construction thereof;

FIG. 3 is an enlarged section taken along lines 3—3 of FIG. 2; and

DETAILED DESCRIPTION OF THE PREFERRED EMBODIMENTS

Figure 4:
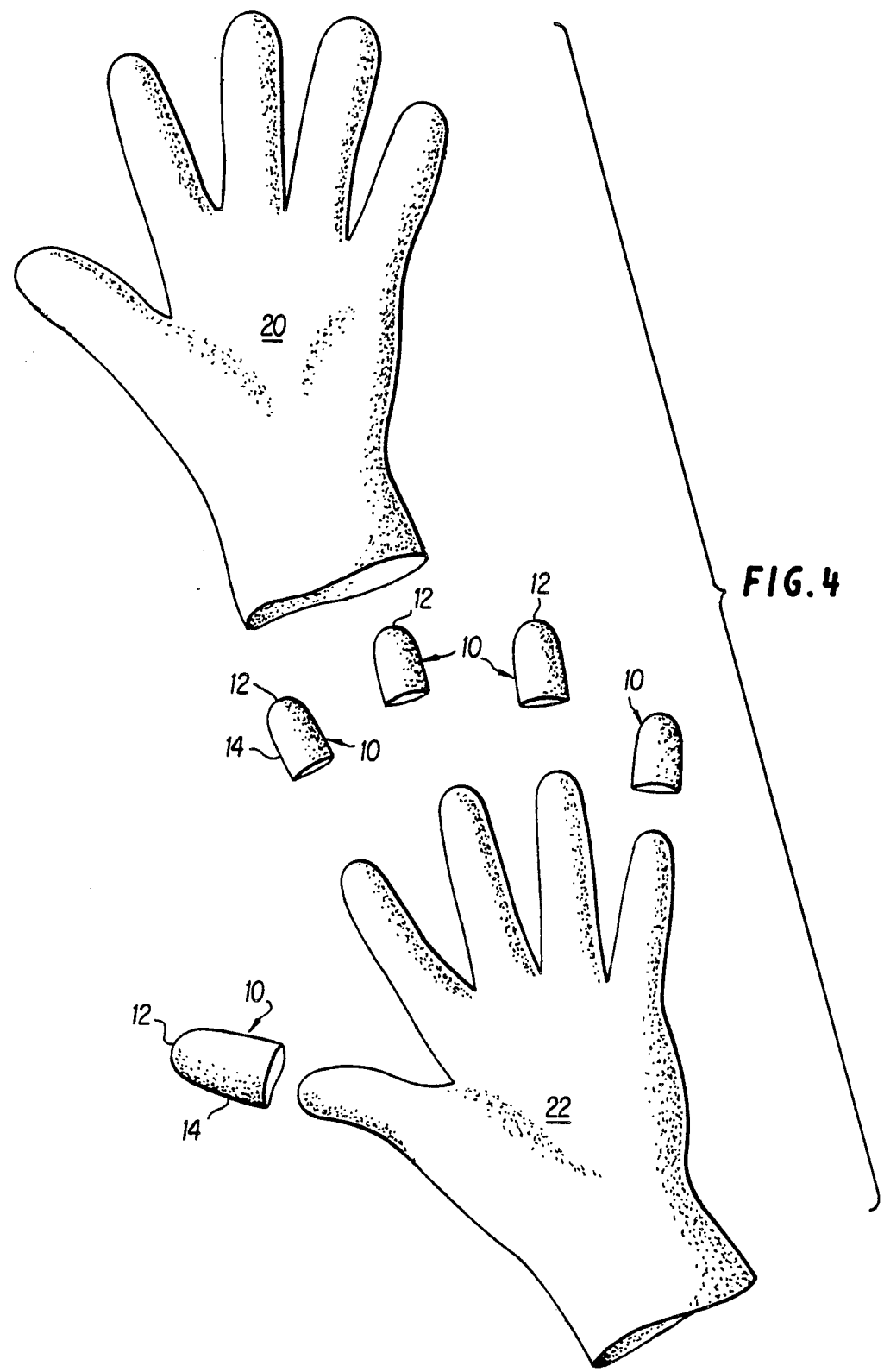
FIG. 4 is an exploded view of the second embodiment of the invention shown in FIG. 2 showing an inner liner, an array of finger pads and an outer layer.

Referring first to the drawings in general where like reference numerals refer to similar structure, heavy rubber dome-shaped and/or curved finger pads 10 of varying size appropriate to the thumb or finger to be covered and of a length substantially less than the length of the finger stall in which the pad is installed are coated, over at least the tip 12 thereof and up to the entire outside surface 14 with an adhesive layer such as, for example, rubber cement 16. After positioning the rubber pads 10 correctly with respect to a glove 18, the pads are inserted into the glove and the adhesive 16 is allowed to set. The glove 18 may in accordance with one use be a seamless, heavy-duty vinyl glove.

Either embodiment of the invention may be used alone, for example, either embodiment could be used in applications that would be appropriate for use of a rubber glove 18 alone but in which the added protection of the rubber finger pads 10 is desirable. Alternatively, the invention may be used as a liner for another type of glove (not shown), for example, as a liner in a burlap-type gardening glove, to reduce injuries to the tips of the fingers and nails.

In the embodiment of FIG. 1, the glove 18 is comprised of a single glove layer 20 with pads 10 inserted in each of the finger stalls. In the embodiment of FIGS. 2–4, the glove 18 is comprised of the single glove layer 20 with the pads 10 inserted in each of the finger stalls as well as an additional inner glove layer 22.

As is best seen in FIG. 3, the outer glove layer 20 is secured to the pad 10 by a first layer of adhesive 26 while the inner glove layer 22 is secured to the pad 10 by a second layer of adhesive 28.

Referring now specifically to the embodiment of FIGS. 2–4, in order to provide a more easily removable glove 18, the layer 20 as described above is made, then the second glove layer 22, which is preferably a thin surgical-type glove which has been coated at the outer tips of the thumb and finger stalls with an adhesive is inserted into the glove of FIG. 1. The finger pads 10 are thus sandwiched between the two glove layers 20 and 22, respectively, with the thin glove 22 disposed on the inner side of the sandwich to form a liner. This embodiment allows for easier removal of the hand from the liner, as well as an additional layer of protection.

As third and fourth alternative embodiments of this invention there may be substituted for a seamless heavy-duty vinyl glove as the outer glove a thinner, surgical-type glove, with or without a similar glove disposed as an inner layer. These embodiments may be especially practical for use when the requirement of flexibility and fine control while wearing the gloves must be balanced against the need for protection from injury. One example is the requirements of the gloves to be worn by medical or clinical laboratory personnel when handling sharps (e.g., needles, lancets, I.V. equipment, scalpels, etc.) or potentially contaminated glassware and plasticware, whether broken or intact.

People in the health professions are especially likely to receive cuts and sticks on the ends of their fingers. Besides the usual possibility of contracting bothersome viral, bacterial and fungal infections as a consequence of environmental contamination of the wound itself, there is an ever increasing awareness and justifiable fear of contracting dangerous, indeed deadly, diseases from contaminated matter present on the sharp point or edge itself. There have been numerous instances documented in which hepatitis and even AIDS has been transmitted to a medical or clinical laboratory worker due to accidental punctures with a contaminated sharp. Due to the type of work these people do, these injuries are most likely to occur at the ends of their fingers. Thus, the present invention provides a much needed improvement for this utility as well, by providing added protection to the ends of the fingers as well as maintaining the flexibility needed to do the precision handwork required in these professions. As before, these embodiments may be used alone or as a liner in conjunction with an outer glove of another type for added protection.

The finger pads 10 may comprise various configurations and materials, so long as they are made of a flexible rubber or other polymeric material which is resistant to penetration by sharp objects and they cover no more than the distal two phalanges of the finger. Exemplary of a preferred embodiment of the finger pad 10 is the "GRIPEEZ" finger pad which is commercially available and prior to this invention was used either alone or on the thumb and index finger for sorting papers.

The outer seamless heavy-duty glove 20 may comprise various materials as well, including vinyl, rubber or other polymeric materials which add resistance to puncture.

For the inner glove 2 in embodiments two and four and the outer glove 20 of embodiment three, there may be used thin vinyl or rubber surgical gloves or thin gloves of other materials. One preferred embodiment comprises gloves 18 in which the inner and optionally outer glove 20 and 22, respectively, are made of materials which are "breathable" in that they allow the passage of air and gases through the glove in order to provide more comfort to the wearer.

For the adhesive, any of a number of well known glues, cements, adhesives and bonding agents may be used, but not limited to adhesives etc., known to those skilled in the art to be compatible with material from which the gloves are comprised.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A protective glove comprising:
   an outer protective layer in the form of a flexible polymeric glove having a plurality of finger stalls of a selected length, the outer protective layer having an inner surface and an outer surface;
   a least one flexible polymeric finger pad of a dome-shaped configuration, installed in a finger stall, said pad being substantially impenetrable to sharp objects, the finger pad having an outer surface, an inner surface and a length substantially less than the length of the finger stall in which the pad is installed, the outer surface of the pad being adhesively secured to the inner surface of the outer protective layer; and optionally
   an inner protective layer in the form of a flexible polymeric glove having a plurality of finger stalls, the inner layer having an inner surface and an outer surface, the outer surface of the inner protective layer being adhesively secured to the inner surface of the flexible polymeric finger pad and in abutment with the inner surface of the outer protective layer.

2. In combination, a protective glove comprising:
   the protective glove of claim 1, worn as a liner, and a second outer glove comprising a material different from at least one of the polymeric materials of said protective glove, wherein the inner finger stalls of the second glove are disposed over the corresponding finger stalls of said protective glove.

3. A protective glove of claim 1, wherein the finger stalls and finger pads are sufficiently long to accommodate fingernails which extend past the distal end of the fingertip.

4. A protective glove of claim 1, wherein the finger pad comprises a polymeric material of sufficient thickness and tensile strength to substantially reduce penetration by foreign objects.

5. A protective glove of claim 4, wherein the finger pad comprises a rubber material.

6. A protective glove of claim 4, wherein the outer protective layer comprises a second polymeric material.

7. A protective glove of claim 6, wherein the second polymeric material is waterproof.

8. A protective glove of claim 7, wherein the second polymeric material is vinyl.

9. A protective glove of claim 2, wherein the inner protective layer comprises a third polymeric material.

10. A protective glove of claim 9, wherein the inner protective layer comprises a thin surgical-type glove.

11. A protective glove of claim 9, wherein the third polymeric material comprises a breathable polymer.

12. A protective glove of claim 9, wherein the second polymeric material of the outer protective layer is the same as the third polymeric material of the inner protective layer.

13. A glove for protecting long fingernails comprising
   an outer protective layer in the form of a flexible polymeric glove having a plurality of finger stalls of a length sufficient to accommodate fingernails which extend past the distal end of the fingertip, the outer protective layer having an inner surface and an outer surface;
   a least one flexible polymeric finger pad of a dome-shaped and curved configuration and of a length at the distal end of the fingertip sufficient to accommodate fingernails which extend past the distal end of the fingertip, installed in a finger stall, said pad being substantially impenetrable to sharp objects, the finger pad having an outer surface, an inner surface and a proximal length substantially less than the length of the finger stall in which the pad is installed, the outer surface of the pad being adhesively secured to the inner surface of the outer protective layer; and optionally an inner protective layer in the form of a flexible polymeric glove having a plurality of finger stalls of a length sufficient to accommodate fingernails which extend past the distal end of the fingertip, the inner layer having an inner surface and an outer surface, the outer surface of the inner protective layer being adhesively secured to the inner surface of the flexible polymeric finger pad and in abutment with the inner surface of the outer protective layer.

* * * * *